(12) United States Patent
Wei et al.

(10) Patent No.: US 7,201,071 B2
(45) Date of Patent: Apr. 10, 2007

(54) WIDE RANGE CONTINUOUS DILUTER

(75) Inventors: Qiang Wei, Novi, MI (US); Ichiro Asano, Konan (JP)

(73) Assignee: Horiba, Ltd., Kyoto (JP)

( * ) Notice: Subject to any disclaimer, the term of this patent is extended or adjusted under 35 U.S.C. 154(b) by 196 days.

(21) Appl. No.: 11/056,716

(22) Filed: Feb. 11, 2005

(65) Prior Publication Data

US 2006/0179960 A1    Aug. 17, 2006

(51) Int. Cl.
  *G01N 1/00* (2006.01)
(52) U.S. Cl. .................................. 73/863.03
(58) Field of Classification Search ............... None
  See application file for complete search history.

(56) References Cited

U.S. PATENT DOCUMENTS

| | | | |
|---|---|---|---|
| 3,975,953 A | 8/1976 | Smith et al. | |
| 4,586,367 A | 5/1986 | Lewis | |
| 5,058,440 A | 10/1991 | Graze, Jr. | |
| 5,090,258 A | 2/1992 | Yamasaki et al. | |
| 5,756,360 A | 5/1998 | Harvey et al. | |
| 6,016,711 A | 1/2000 | Ullman et al. | |
| 6,062,092 A | 5/2000 | Weaver | |
| 6,200,819 B1 | 3/2001 | Harvey et al. | |
| 6,615,677 B2 | 9/2003 | Dickson et al. | |
| 6,729,195 B2 | 5/2004 | Graze, Jr. | |

*Primary Examiner*—Robert Raevis
(74) *Attorney, Agent, or Firm*—Brooks Kushman P.C.

(57) ABSTRACT

A wide range continuous diluter for diluting gases that contain small particles to allow subsequent measurement of the diluted gases with an instrument is provided. A dilution gas inlet receives a dilution gas, and a sample gas inlet receives a sample gas. A flow meter measures the sample gas flow rate. A mixer receives and mixes the dilution gas and the sample gas at a dilution ratio. An instrument flow outlet provides a well-defined flow into the instrument from the mixture flow. A make-up gas inlet is arranged to provide make-up gas into the mixture flow at a controlled rate. Because the dilution gas flows at a controlled rate and the mixture flows at a controlled rate, changing the flow rate of the make-up gas causes a responsive change in the sample gas flow rate, thereby allowing continuous adjustment and control of the dilution ratio when desired.

17 Claims, 2 Drawing Sheets

WIDE RANGE CONTINUOUS DILUTER

BACKGROUND OF THE INVENTION

1. Field of the Invention

The invention relates to diluting engine exhaust or other gases that contain small particles.

2. Background Art

In order to characterize engine exhaust particulate matter (PM) emissions, it is required that the engine exhaust be diluted. Because the engine emits a high concentration of particles, the engine exhaust must be diluted with a high dilution ratio (typically greater than 100:1) to reach the measurable range of certain particle number instruments. The number concentration of engine exhaust particles may vary in a wide range. This is due to the variety of engine technologies and operating conditions. To satisfy these requirements and obtain accurate results, wide range dilution capability is required.

The typical traditional partial flow diluter controls dilution air flow and total mixture flow with mass flow controllers. The sample flow is calculated by subtracting the dilution air flow from the total mixture flow. The dilution ratio is calculated by dividing the total mixture flow by the calculated sample flow. At low dilution conditions, this approach provides an accurate dilution ratio calculation.

As the dilution ratio increases, the accuracy of the calculated dilution ratio drops due to the uncertainties of the total flow and dilution air flow measurements. This results in inaccurate characterization of the emissions. Therefore, use of dilution systems employing the typical traditional partial flow diluter has been limited to somewhat lower dilution ranges, such as 40:1 or lower.

For the foregoing reasons, there is a need for an improved diluter.

SUMMARY OF THE INVENTION

It is an object of the invention to provide an accurate approach to diluting engine exhaust, and other gases that contain small particles, with wide range dilution capabilities.

It is another object of the invention to provide a diluter that maintains accuracy under high dilution conditions.

The invention contemplates an improved partial flow diluter. The wide range continuous diluter of the invention allows variation of the dilution ratio, in preferred embodiments, from 1:1 to over 1000:1. The dilution ratio can be controlled continuously in a wide range by changing the flow rate of a small make-up flow introduced after mixing, that causes the rate of the sample flow to change. The sample flow is measured directly, and the diluter provides a highly accurate dilution ratio over the operating range due to the sample flow being measured directly.

In carrying out the invention, a wide range continuous diluter is provided. The diluter comprises a dilution air inlet, a sample gas inlet, and a mixer for mixing the dilution air and the sample gas. The diluter further includes a mixture outlet for receiving the mixture flow from the mixer. The total mixture flow is controlled by, for example, a critical orifice or mass flow controller. The dilution air flow is controlled by, for example, a mass flow controller. A well-defined flow (constant or variable) flows to the measuring instrument from the mixture flow.

A flow of make-up air is provided to the total mixture flow, after the mixer. In this way, by changing the flow rate of the make-up air, the sample flow rate is changed as well. This approach allows continuous adjustment of the dilution ratio. The dilution ratio can be adjusted over a wide range. The sample flow is measured, for example, with an orifice flow meter. As a result, the calculated dilution ratio is accurate over a wide dilution range.

If desired for a particular application, a feedback control loop may control the dilution ratio. For example, when the system requires a constant dilution ratio, a proportional/integral/derivative (PID) loop may be employed to control the dilution ratio by manipulating the make-up air flow.

Further, it is appreciated that, in a preferred embodiment, the sample flow rate is measured by an orifice flow meter. In this case, particle losses over the orifice flow meter can be ignored. Accurate detection of the pressure drop across the orifice flow meter is assured by applying different orifice flow meters per the dilution ratio. The most appropriate flow meter can be chosen automatically or manually.

In another aspect of the invention, to minimize the small particle losses at high dilution ratio, the invention comprehends using a by-pass flow upstream of the orifice flow meter to reduce the residence time of the flow in the transfer line.

DETAILED DESCRIPTION OF THE PREFERRED EMBODIMENT

Figure 1:
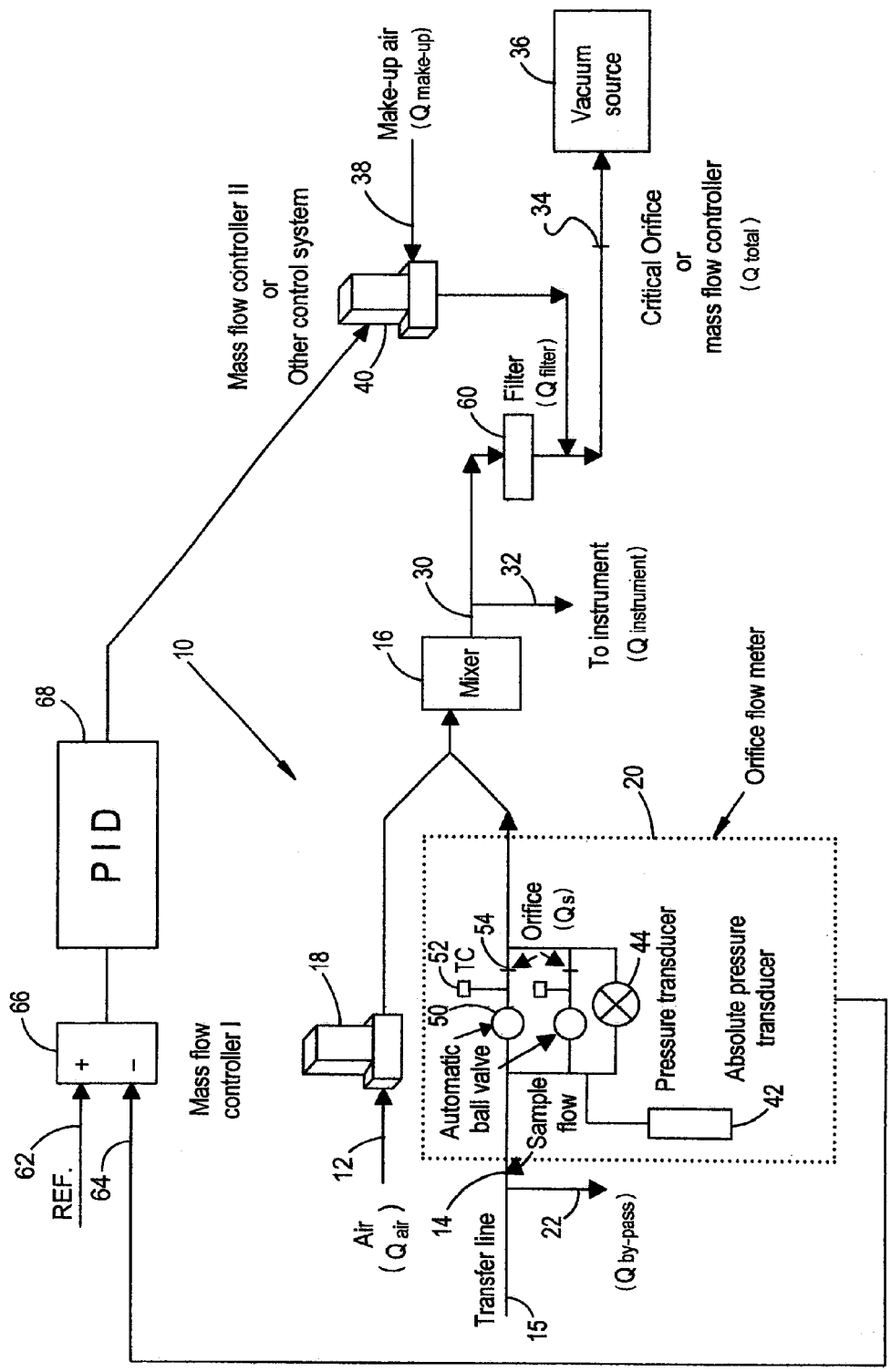
FIG. 1 is a wide range continuous diluter made in accordance with a preferred embodiment of the invention.

In FIG. 1, the preferred embodiment of the wide range continuous diluter is generally indicated at 10. A dilution gas inlet 12 receives a dilution gas, and a sample gas inlet 14 receives a sample gas. A mixer 16 is connected to dilution gas inlet 12 and sample gas inlet 14 for receiving and mixing the gases at a dilution ratio. The flow rate of the dilution gas is controlled by mass flow controller 18. Orifice flow meter 20 measures the sample gas flow rate. By-pass flow outlet 22 is provided upstream of flow meter 20 to reduce the residence time of the sample gas flow through the transfer line 15, which connects inlet 14 to the expected sampling source, for example, engine exhaust.

Mixer 16 has outlet 30, and instrument flow outlet 32 is arranged to provide a well-defined flow into the instrument. The gas mixture flows at a controlled rate provided by critical orifice 34 and vacuum source 36. Critical orifice 34 may alternatively be a mass flow controller. Make-up gas inlet 38 provides make-up gas into the gas mixture flow controlled by mass flow controller 40.

With continuing reference to FIG. 1, orifice flow meter 20 includes absolute pressure transducer 42, pressure transducer 44, and a plurality of differently sized orifice flow meters. Each orifice flow meter includes a valve 50, a thermocouple 52, and an orifice 54. When engine particulate matter (PM) mass measurement is required, a pre-weighted filter 60 and holder is installed upstream of the make-up air.

A feedback control loop controls the dilution ratio in this embodiment by varying the make-up gas flow such that the dilution ratio tracks a desired value. More specifically, feedback signal 64 is compared to reference signal 62 at summer 66 to produce an error signal. PID control 68, based on the error signal, determines the command signal for mass flow controller 40. In this way, it is possible to track to a constant dilution ratio or any other suitable reference signal.

In operation, there are six flows. All flow rates in the following description are at the same conditions, either the standard or reference conditions. $Q_{by\text{-}pass}$ is the by-pass flow upstream of the orifice 54. The purpose of the by-pass flow is to minimize the residence time of the sample flow before entering the flow meter 20. The particle losses for small particles (less than 20 nanometers) by diffusion mechanism are minimized in the sampling line. $Q_{total}$ is the total mixture flow in the system. $Q_{total}$ is controlled as a constant by critical orifice 34, or a mass flow controller. $Q_{air}$ is the particle free dilution air flow, and is controlled as a constant by mass flow controller 18. $Q_s$, is the sample flow and is measured by orifice flow meter 20 in real-time. $Q_{make\text{-}up}$ is the make-up air flow. The make-up air flow can be adjusted, and the flow rate is controlled by mass flow controller 40. In normal operations, $Q_{make\text{-}up}$ is much smaller than $Q_{air}$. However, under some conditions, $Q_{make\text{-}up}$ can be larger than $Q_{air}$. $Q_{instrument}$ is the flow into the instrument or filter, that is well-defined and can be either constant or varied.

The sample flow and the dilution air or gas are mixed in mixer 16. Mixer 16 provides the uniform mixing of the sample flow and dilution air. Since flows of the dilution air and the sample flow are measured upstream of mixer 16 any kind of mixer can be used in the system. In some applications, hot dilution air is required. A heating system could be installed to heat the dilution air and the mixer for such applications.

The flow in the diluter can be defined as:

$$Q_{total} = Q_{air} + Q_s + Q_{make\text{-}up} - Q_{instrument} \qquad (1)$$

In this illustrated preferred embodiment, the total flow and the dilution air flow are maintained as constants during operation.

By adjusting make-up air flow $Q_{make\text{-}up}$, total flow $Q_{total}$ will remain constant. As a result, sample flow $Q_s$ is changed. For example, while the make-up air flow is increased, the sample flow will decrease to maintain the constant total flow; in the opposite, while the make-up air flow is decreased, the sample flow will increase to maintain the constant total flow.

The dilution ratio (DR) can be defined as:

$$DR = \frac{Q_{air} + Q_s}{Q_s} = 1 + \frac{Q_{air}}{Q_s} \qquad (2)$$

Because the dilution air flow does not change, the dilution ratio is a function of the sample flow only. When the sample flow is decreased with the increase of the make-up flow, the dilution ratio increases. In the opposite case, when the sample flow is increased with the decrease of the make-up flow, the dilution ratio decreases.

Since the make-up air is adjusted continuously, the sample flow is changed continuously. As a result, the dilution ratio is continuously controlled. A 1:1 ratio can be achieved without the dilution air flow ($Q_{air}=0$).

The sample flow $Q_s$ is measured by orifice flow meter 20 which includes multiple internal flow meters. Each internal flow meter includes a thermocouple 52, an orifice 54, and a valve 50. In operation, the valves are manipulated to select the appropriate internal flow meter. When the sample flow $Q_s$ is changed, the pressure drop across orifice 54 changes as well. The pressure drop is measured by pressure transducer 44. To maintain an accurate pressure measurement from pressure transducer 44, when the system runs under high dilution ratio (for example, greater than 100:1 and with a small sample flow rate), the internal flow meter with a smaller orifice will be chosen. The orifice selection process is controlled either automatically or manually. As shown, orifice flow meter 20 includes a pair of internal flow meters.

The flow rate through an orifice is calibrated as a function of the pressure difference over the orifice at the standard or reference conditions. The calibrated curve is generated by a precise flow meter, and expressed as a polynomial equation. For pressure differences that are not specifically calibrated, these flow rates can be calculated with the equation.

During operation, the sample flow temperature and pressure may not be at the standard or reference conditions. Absolute pressure transducer 42 and a thermocouple 52 measure the absolute pressure and temperature of the sample flow, respectively. Then, the sample flow can be corrected to the standard or reference conditions. A corrected sample flow is used in the above mentioned equation (Equation 2) to obtain the dilution ratio.

With continuing reference to FIG. 1, the system is equipped with a PID control system to provide stable dilution ratios. If a constant dilution ratio is required during operation, the PID control system will be activated. The PID controller adjusts the make-up air to achieve the constant sample flow. As a result, constant dilution ratios are obtained. In FIG. 1, orifice flow meter 20 provides a feedback signal 64 that is compared with reference signal 62 at summer 66. The resulting error signal is processed by PID controller 68, which determines the command signal for mass flow controller 40.

In some applications, it may be required to check if there are particles in the system when the sample flow is turned off. This test is called zero check.

The diluter 10 provides a unique way to do zero check. By adjusting the make-up air to be large enough, it is possible to cause the sample flow to flow in an opposite direction to keep the constant total flow. As a result, there is no sample flow into the instrument. With this approach, the instrument can detect if there are leaks in the system or particles in the dilution air.

When engine particulate matter (PM) mass measurement is required at the same time as the number or size measurement, a pre-weighted filter and holder are installed upstream of the make-up air, as shown in FIG. 1 at 60. The flow $Q_{filter}$ flowing through filter 60 is expressed as:

$$Q_{filter} = Q_{air} + Q_s - Q_{instrument}$$

This measurement can also be obtained alone without running the number or size measurement simultaneously.

Figure 2:
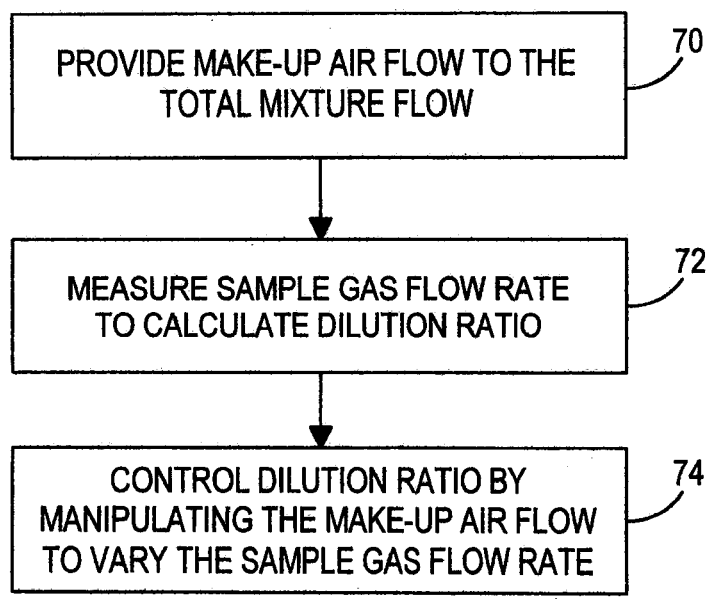
FIG. 2 is a block diagram illustrating a method in a preferred embodiment of the invention.

In FIG. 2, a preferred method of operating diluter 10 is illustrated. At block 70, make-up airflow is provided to the total mixture flow. At block 72, the sample gas flow rate is measured to calculate the dilution ratio. At block 74, the dilution ratio is controlled by manipulating the make-up airflow to vary the sample gas flow rate.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A wide range continuous diluter for diluting gases that contain small particles to allow subsequent measurement of the diluted gases with an instrument, the diluter comprising:

a dilution gas inlet for receiving a dilution gas at a controlled rate;

a sample gas inlet for receiving a sample gas;

a flow meter for measuring the sample gas flow rate;

a mixer connected to the dilution gas inlet and to the sample gas inlet for receiving and mixing the dilution gas and the sample gas at a dilution ratio, the mixer having an outlet for providing a mixture flow at a controlled rate;

an instrument flow outlet arranged to provide a well-defined flow into the instrument from the mixture flow;

a make-up gas inlet arranged to provide make-up gas into the mixture flow at a controlled rate; and whereby changing the flow rate of the make-up gas causes a responsive change in the sample gas flow rate, thereby allowing continuous adjustment of the dilution ratio.

2. The diluter of claim 1 wherein the mixture flow rate is controlled by a critical flow orifice.

3. The diluter of claim 1 wherein the mixture flow rate is controlled by a mass flow controller.

4. The diluter of claim 1 wherein the dilution gas flow rate is controlled by a mass flow controller.

5. The diluter of claim 1 wherein the flow meter for measuring the sample gas flow rate comprises an orifice flow meter.

6. The diluter of claim 1 wherein the flow meter for measuring the sample gas flow rate comprises a plurality of differently sized orifice flow meters, and wherein the orifice flow meter applied to the sample gas flow depends on the dilution ratio.

7. The diluter of claim 1 further comprising:

a feedback control loop for controlling the dilution ratio by varying the make-up gas flow such that the dilution ratio tracks a desired value.

8. The diluter of claim 7 wherein the feedback control loop utilizes proportional/integral/derivative control.

9. The diluter of claim 7 wherein the feedback control loop is configured to track a constant dilution ratio.

10. The diluter of claim 1 wherein the flow into the instrument is a constant instrument flow.

11. The diluter of claim 1 wherein the flow into the instrument is a well-defined variable instrument flow.

12. The diluter of claim 1 further comprising:

a by-pass flow outlet upstream of the flow meter to reduce the residence time of the sample gas flow in a transfer line connecting the sample gas inlet to the sampling source.

13. The diluter of claim 1 further comprising:

a filter located upstream of the make-up gas inlet.

14. A method of using the wide range continuous diluter of claim 1, the method comprising:

controlling the make-up gas flow rate to cause an outward flow from the sample gas inlet; and obtaining the measurement from the instrument.

15. A method of using the wide range continuous diluter of claim 1, the method comprising:

adjusting the make-up gas flow rate to cause a responsive change in the sample gas flow rate.

16. The method of claim 15 wherein the make-up gas flow rate is adjusted such that the dilution rate tracks a desired value.

17. The method of claim 16 wherein the desired value is a constant dilution rate.

* * * * *